United States Patent
Jialanella et al.

(10) Patent No.: US 8,304,543 B2
(45) Date of Patent: Nov. 6, 2012

(54) BLOCKING AGENTS FOR ORGANOBORANE COMPOUNDS

(75) Inventors: Gary Lee Jialanella, Oxford, MI (US); Shaoguang Feng, Shanghai (CN); Peter N. Nickias, Midland, MI (US); Toni Ristoski, Rochester Hills, MI (US)

(73) Assignee: Dow Global Technologies LLC, Midland, MI (US)

( * ) Notice: Subject to any disclaimer, the term of this patent is extended or adjusted under 35 U.S.C. 154(b) by 467 days.

(21) Appl. No.: 12/603,381

(22) Filed: Oct. 21, 2009

(65) Prior Publication Data

US 2010/0105910 A1 Apr. 29, 2010

Related U.S. Application Data

(60) Provisional application No. 61/107,947, filed on Oct. 23, 2008.

(51) Int. Cl.
*C07F 5/02* (2006.01)

(52) U.S. Cl. ....................................... 546/13

(58) Field of Classification Search .................... 546/13
See application file for complete search history.

(56) References Cited

U.S. PATENT DOCUMENTS

| | | |
|---|---|---|
| 3,275,611 A | 9/1966 | Mottus et al. |
| 4,538,920 A | 9/1985 | Drake |
| 5,082,147 A | 1/1992 | Jacobs |
| 5,106,928 A | 4/1992 | Skoultchi et al. |
| 5,143,884 A | 9/1992 | Skoultchi et al. |
| 5,286,821 A | 2/1994 | Skoultchi |
| 5,310,835 A | 5/1994 | Skoultchi et al. |
| 5,376,746 A | 12/1994 | Skoultchi |
| 5,539,070 A | 7/1996 | Zharov et al. |
| 5,616,796 A | 4/1997 | Pocius et al. |
| 5,621,143 A | 4/1997 | Pocius |
| 5,681,910 A | 10/1997 | Pocius |
| 5,686,544 A | 11/1997 | Pocius |
| 5,690,780 A | 11/1997 | Zharov et al. |
| 5,691,065 A | 11/1997 | Zharov et al. |
| 5,718,977 A | 2/1998 | Pocius |
| 5,795,657 A | 8/1998 | Pocius et al. |
| 6,806,330 B1 | 10/2004 | Sonnenschein et al. |

OTHER PUBLICATIONS

Int'l App. No. PCT/US09/061529, Int'l Filing Date Oct. 21, 2009 International Search Report dated Jan. 19, 2010.

*Primary Examiner* — Charanjit Aulakh

(57) ABSTRACT

An organoborane complex is disclosed. The complex includes a blocking agent comprising a bifunctional Lewis base. The blocking agents include an amine group and a second functional group that has a lower Lewis basicity than the first functional group. The blocking is based on amino alkyl pyridines.

3 Claims, 2 Drawing Sheets

BLOCKING AGENTS FOR ORGANOBORANE COMPOUNDS

CROSS-REFERENCE TO RELATED APPLICATION

This application claims the benefit of U.S. Provisional Application No. 61/107,947 filed Oct. 23, 2008. The disclosure of the above application is incorporated herein by reference.

FIELD OF THE INVENTION

This invention relates to blocking agents used in organoborane complexes. Such complexes are useful as free radical polymerization initiators and in polymerizable compositions comprising compounds containing moieties capable of free radical polymerization and organoborane amine complex initiators of the invention. The organoborane complexes are also useful in adhesive, sealant, coating and ink compositions containing organoborane amine complexes and compounds containing moieties capable of free radical polymerization.

BACKGROUND OF THE INVENTION

In many practical situations in which compounds are subjected to polymerization or where adhesives are used, it is desirable to have polymerizable compositions and adhesive compositions which can cure on demand. Cure on demand means that the polymerization can be initiated when desired. A significant problem with cure on demand compositions is the stability of the compositions. Many such compositions will begin curing at, or near, ambient temperature or will partially cure at ambient temperature resulting in an increased viscosity causing difficulties in handling and reduced functionality of the polymerizable composition or adhesive composition.

Low surface energy olefins such as polyethylene, polypropylene and polytetrafluoroethylene have a variety of attractive properties in a variety of uses, such as for toys, automobile parts, furniture applications and the like. Because of the low surface energy of these plastic materials, it is very difficult to find adhesive compositions which bond to these materials. The commercially available adhesives which are used for these plastics require time consuming or extensive pretreatment of the surface before the adhesive will bond to the surface. Such pretreatments include corona treatment, flame treatment and the like. The requirement for extensive pretreatment of the surface results in significant limitations to the designers of automobile components, toys, furniture and the like. It is desirable to have adhesive compositions which are capable of bonding to low surface energy substrates, and bonding low surface energy substrates to other substrates, without the need for extensive or costly pretreatment.

Organoborane compounds exhibit good adhesion to low surface energy olefins. Organoborane compounds are, however, pyrophoric in air and are very reactive in methacrylate adhesive systems. Organoborane compounds can be stabilized by complexing them with a blocking agent. The blocking agents prevent pyrophoric reactions of the organoborane compounds as well reducing curing of compositions at or near ambient temperatures before desired.

Sonnenschein et al, U.S. Pat. No. 6,806,330 discloses amine organoborane complex polymerization initiators and polymerizable compositions. The amine acts as a blocking agent to stabilize the compositions. The amine is an amine having an amidine structural component; an aliphatic heterocycle having at least one nitrogen in the heterocyclic ring wherein the heterocyclic compound may also contain one or more nitrogen atoms, oxygen atoms, sulfur atoms, or double bonds in the heterocycle; a primary amine which in addition has one or more hydrogen bond accepting groups wherein there is at least two carbon atoms, preferably three, between the primary amine and the hydrogen bond accepting group, such that due to inter- or intramolecular interactions within the complex the strength of the B—N bond is increased; or a conjugated imine. Preferred hydrogen bond accepting groups include the following: a secondary amine, a tertiary amine, an ether, a halogen, a polyether group or a polyamine group. The complexes of the invention are used in polymerizable compositions, adhesive compositions and coatings compositions containing compounds having moieties which polymerize under free radical polymerization conditions.

Mottus et al., U.S. Pat. No. 3,275,611 discloses a process for polymerizing olefinic compounds with a catalyst comprising an organoborane compound, a peroxygen compound and an amine. It is disclosed that the organoborane compound and amine may be added to the reaction mixture separately or as a preformed complex, and that the complex is preferred. The presence of the amine in the complex reduces the pyrophoricity of the organoborane in air. Among the amine complexing agents disclosed are pyridine, aniline, toluidine, dimethylbenzylamine, and nicotine. Many of the complexes disclosed in Mottus are pyrophoric at all amine to boron atom ratios. In addition, many of the amine complexes do not display significant adhesive properties when applied to low surface energy substrates.

A series of patents issued to Skoultchi (U.S. Pat. Nos. 5,106,928, 5,143,884, 5,286,821, 5,310,835 and 5,376,746) disclose a two-part initiator system that is reportedly useful in acrylic adhesive compositions. The first part of the two-part system includes a stable organoborane-amine complex and the second part includes a destabilizer or activator such as an organic acid or an aldehyde. The organoborane compound of the complex has three ligands which can be selected from $C_{1-10}$ alkyl groups or phenyl groups. Useful amines disclosed include octylamine, 1,6 diaminohexane, diethylamine, dibutylamine, diethylenetriamine, dipropylenediamine, 1,3 propylene diamine, and 1,2 propylene diamine. The adhesive compositions are disclosed to be useful in structural and semi-structural adhesive applications, such as speaker magnets, metal to metal bonding, automotive glass to metal bonding, glass to glass bonding, circuit board component bonding, bonding select plastics to metal, glass to wood, etc. and for electric motor magnets.

Zharov et al. discloses in a series of U.S. Pat. Nos. (5,539,070; 5,690,780; and 5,691,065) polymerizable acrylic compositions which are particularly useful as adhesives wherein organoborane amine complexes are used to initiate cure. The organoboranes used have three ligands attached to the borane atom which are selected from $C_{1-10}$ alkyl groups and phenyl. The amine is an alkanol amine or a diamine where the first amine group can be a primary or secondary amine and the second amine is a primary amine. It is disclosed that these complexes are good for initiating polymerization of an adhesive which bonds to low surface energy substrates.

Pocius in a series of patents (U.S. Pat. Nos. 5,616,796; 5,621,143; 5,681,910; 5,686,544; 5,718,977; and 5,795,657) disclose amine organoborane complexes with a variety of amines such as polyoxyalkylene polyamines and polyamines which are the reaction product of diprimary amines and compound having at least two groups which react with a primary amine.

Many of the complexes disclosed in the Zharov, Skoultchi and Pocius Patents are not stable in compositions containing olefinic unsaturation at, or near, ambient temperatures and thus the complexes disassociate and induce polymerization at, or near, ambient temperature with time. This instability at, or near, ambient temperature can result in polymerization before desired and can result in compositions which are unsuitable for the desired use.

Therefore, there is a desire for an improved blocking agent that can be used in an organoborane complex for use in initiator systems for free radical polymerization which are safe to handle, not pyrophoric, which can be used to form cure on demand polymer systems or can be used in adhesive systems which cure on demand. Such improved blocking agents can also be used in adhesive systems which are capable of bonding to low surface energy substrates, and initiator systems which facilitate such bonding. In addition to such needs, the complexes need to be thermally stable, that is do not disassociate at, or near, ambient temperatures and thereby initiate polymerization before desired. What is further desired is an improved blocking agent for an organoborane complex that can be used in polymer compositions and adhesive systems which are thermally stable at, or near, ambient temperatures and which will undergo polymerization when the user desires.

SUMMARY OF THE INVENTION

According to one embodiment, there is provided a blocking agent comprising a bifunctional Lewis base.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE PREFERRED EMBODIMENTS

The following description of the preferred embodiment(s) is merely exemplary in nature and is in no way intended to limit the invention, its application, or uses.

Embodiments of the present invention include organoborane complexes. In one embodiment, an organoborane compound forms a complex with a bifunctional Lewis base. The organoborane compound used in the complex may be an alkyl borane. The alkyl borane may be a trialkyl borane or an alkyl cycloalkyl borane. Preferably such borane corresponds to Formula 1:

  Formula 1 wherein B represents Boron; and $R^2$ is separately in each occurrence a $C_{1-10}$ alkyl, $C_{3-10}$ cycloalkyl, or two or more of $R^2$ may combine to form a cycloaliphatic ring. Preferably $R^2$ is $C_{1-4}$ alkyl, even more preferably $C_{2-4}$ alkyl, and most preferably $C_{3-4}$ alkyl. Among the preferred organoboranes are tri-ethyl borane (TEB), tri-isopropyl borane and tri-n-butylborane (TNBB).

To prepare thermally stable polymerizable compositions, thermally stable complexes which do not disassociate, at or near, ambient temperature until desired. The key to preparation of such complexes is the selection of the blocking agent. The blocking agent stabilizes the organoborane. The desirability of the use of a given blocking agent in organoborane complex can be calculated from the energy difference between the Lewis acid-base complex and the sum of energies of the isolated Lewis acid (organoborane) and base known as binding energy. The higher the binding energy the more stable the complex.

Figure 3:
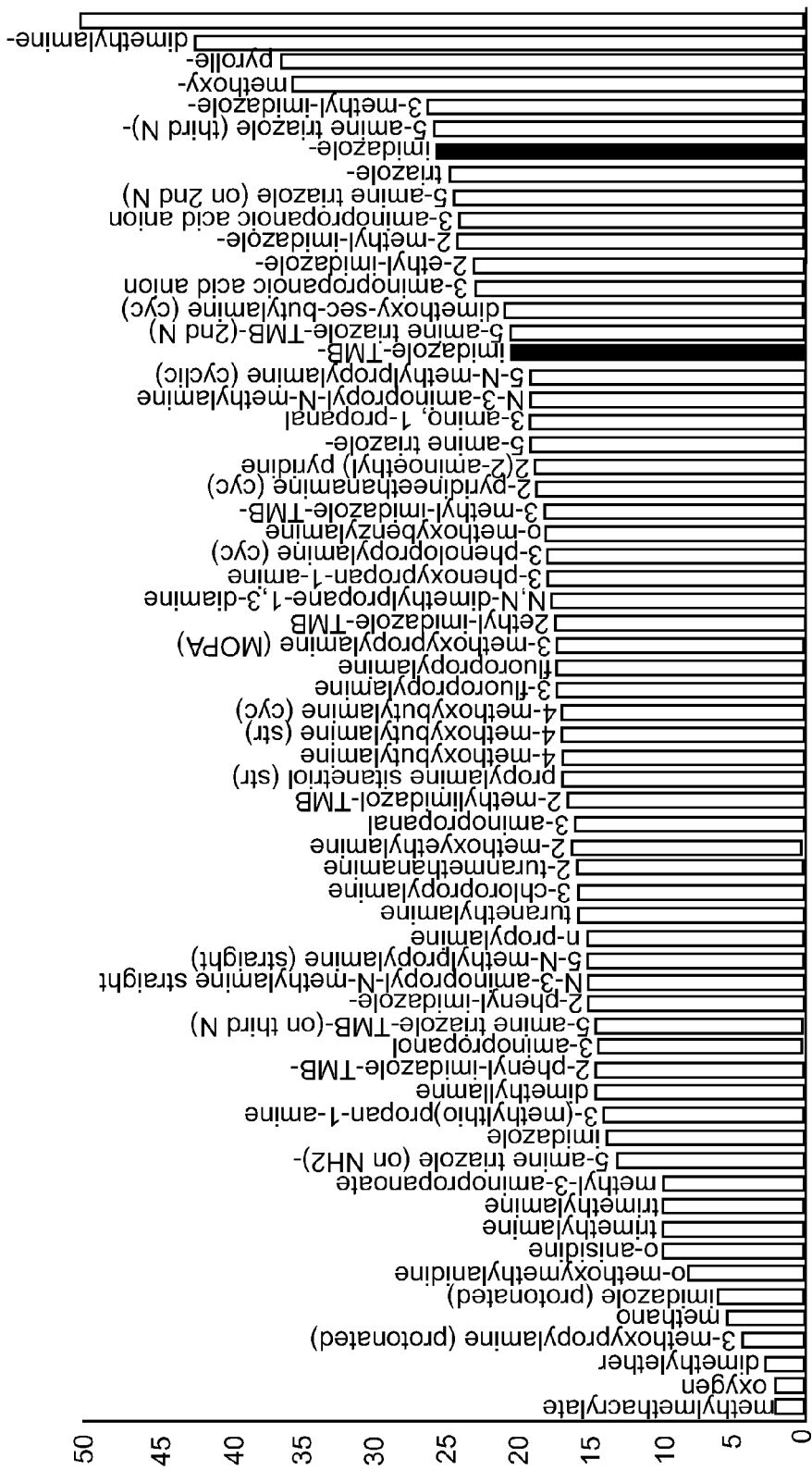
FIG. 3 is a graph showing calculated complex energies for various blocking agents.

Such binding energies can be calculated using theoretical ab-initio methods such as the Hartree Fock method and the 3-21 G basis set. These computational methods are available commercially employing commercial software and hardware such as SPARTAN and GAUSSIAN 98 programs with a Silicon Graphics workstation. Blocking agents having binding energies with organoboranes of ten kilocalories per mol or greater are preferred, blocking agents having a binding energy of 15 kilocalories per mol or greater are more preferred. In the embodiment where polymerization of the compositions of the invention is initiated by use of a decomplexing agent the binding energy of the blocking agent to the organoborane is preferably about 50 kcal/mole or less and most preferably about 30 kcal/mole or less. In the embodiment where polymerization of the compositions of the invention is initiated by use of heat the binding energy of the blocking agent is preferably about 100 kcal/mole or less, more preferably about 80 kcal/mole or less and most preferably about 50 kcal/mole or less. Binding energies of various blocking agent are shown in FIG. 3.

In one embodiment, the blocking agent comprises a bifunctional Lewis base. That is, the Lewis base preferably has two functional groups. One functional group is preferably an amine group. The second functional group has a lower Lewis basicity than the amine group. Further, it is preferred that the functional groups are separated by two to four atoms. The reduced Lewis basicity of the second functional group can be achieved in at least three ways: (1) the second functional group is part of an aromatic ring; (2) the second functional group has bulky alkyl group; and (3) the groups have dissimilar functional groups in which the second functional group has a lower Lewis basicity that the first functional group.

Accordingly, both functional groups can be based on nitrogen when the second functional group is either incorporated into an aromatic ring or when the second functional group has a lower Lewis basicity as a result of steric hindrance due to bulky alkyl groups on or around the nitrogen atom.

The bifunctional Lewis acid may be an amino alkyl pyridine. In one embodiment, the first functional group is an amine. Most preferably, the amine is a primary amine. The hydrogen bonding between the organic substituent of the primary amine undergoes hydrogen bonding with the second functional group. The organic substituent of the primary amine along with the second functional group forms a cyclization ring. Preferably the cyclization ring has between four and eight members. In the most preferred embodiment, the cyclization ring has six members. A six member cyclization ring has the lowest energy state. The second functional group is separated from the amine group by two to four atoms.

In one embodiment, the second functional group may be pyridine. In this embodiment, one to two of the atoms separating the groups can be part of the aromatic ring.

While the second functional group is discussed to be based on nitrogen, it will be appreciated that the heteroatom of the second functional group may be any atom with a lone pair of electrons. These include, for example, oxygen and sulfur.

In one embodiment, the blocking agent comprises an amino alkyl pyridine corresponding to Formula 2:

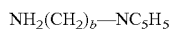
NH$_2$(CH$_2$)$_b$—NC$_5$H$_5$     Formula 2 where b is an integer between 2 and 4.

Among the preferred amines according to Formula 2 is ethylamine. Thus a preferred blocking agent for use with the organoborane is 2(2-aminoethyl)pyridine according to Formula 3:

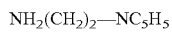
NH$_2$(CH$_2$)$_2$—NC$_5$H$_5$     Formula 3

An organoborane complex incorporating a preferred blocking agent corresponds to:

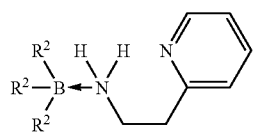

As indicated, internal cyclization occurs with the amine and the pyridine. This internal cyclization is a key feature in the molecular architecture of the blocking agent.

The second functional group described above is pyridine. Additional functional groups based on nitrogen may include pyridines, pyrimidines, pyrazines, pyridazines, triazines, pyrrols, imidazols and indoles. Accordingly, suitable blocking agents may include:

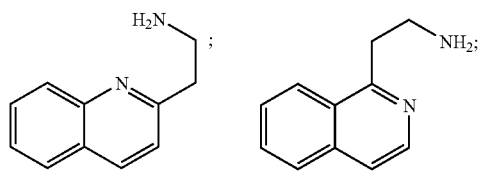

2-(quinolin-2-yl) ethanamine     2-(isoquinolin-1-yl) ethanamine

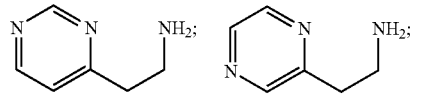

2-(pyrimidin-4-yl) ethanamine     2-(pyrazin-2-yl) ethanamine

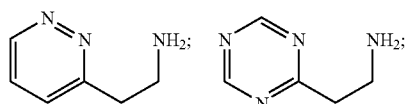

2-(pyridazon-3-yl) ethanamine     2-(1,3,5-triazin-2-yl) ethanamine

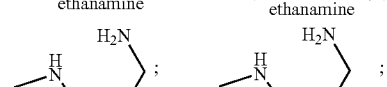

2-(1H-pyrrol-2-yl) ethanamine     2-(1H-imidazol-5-yl) ethanamine

-continued

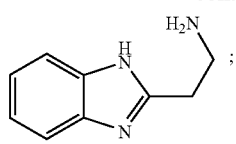

2-(1H-benzo[d]imidazol-2-yl) ethanamine

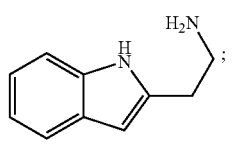 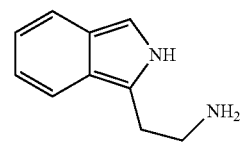

2-(1H-indol-2-yl) ethanamine     2-(2H-isoindol-1-yl) ethanamine

While the second functional group is discussed to be based on nitrogen, it will be appreciated that the heteroatom of the second functional group may be any atom with a lone pair of electrons. These include, for example, oxygen, sulfur and phosphorus.

Examples of second functional groups based on oxygen include furans. Accordingly, suitable blocking agents may include:

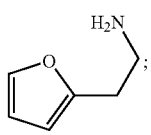

2-(furan-2-yl)ethanamine

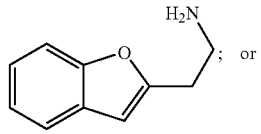

2-(benzofuran-2-yl)ethanamine

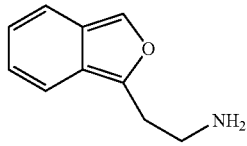

2-(isobenzofuran-1-yl)ethanamine

Examples of second functional groups based on sulfur include thiophenes and thiazols. Accordingly, suitable blocking agent may include:

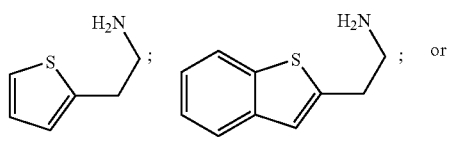

2-(thiophen-2-yl) ethanamine     2-(benzo[b]thiophen-2-yl) ethanamine

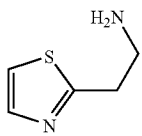

2-(thiazol-2-yl)
ethanamine

Examples of second functional groups based on phosphorus include phosphinines. Accordingly, a suitable blocking agent may include:

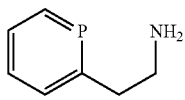

2-(phosphinin-2-yl)ethanamine

Without being bound to a specific theory of operation, it is believed that stability of the complex is enhanced as a result of a combination of the hydrogen bonding effect between the heteroatom of the second functional group with the hydrogen of the first functional group along with the effect achieved as a result of electron delocalization (or distribution) along the aromatic ring. That is, the effects of the hydrogen bonding as a result of internal cyclization and the electron delocalization resulting from the aromatic ring combine to enhance the stability of the complex. These effects enhance the inter- or intramolecular interaction within the complex such that the strength of the B-blocking agent bond is increased. The increased stability results in, inter alia, increased shelf life of the organoborane.

The molar ratio of the blocking agent to the organoborane compound in the complex is relatively important. In some complexes if the molar ratio of blocking agent to the organoborane compound is too low, the complex is pyrophoric. Preferably the molar ratio of blocking agent to organoborane compound is from about 1.0:1.0 to about 3.0:1.0. Below the ratio of about 1.0:1.0 there may be problems with polymerization, stability of the complex and for adhesive uses, adhesion. Greater than about a 3.0:1.0 ratio may be used although there is no benefit from using a ratio greater than about 3.0:1.0. If too much blocking agent is present, this may negatively impact the stability of the adhesive or polymer compositions. Preferably the molar ratio of blocking agent compound to organoborane compound is from about 2.0:1.0 to about 1.0:1.0.

Polymerizable compounds which may contain organoborane complexes as described herein include any monomers, oligomers, polymers or mixtures thereof which contain olefinic unsaturation which can polymerize by free radical polymerization. Such compounds are well known to those skilled in the art. Mottus, U.S. Pat. No. 3,275,611, provides a description of such compounds at column 2, line 46 to column 4, line 16, incorporated herein by reference. Among preferred classes of compounds i=containing olefinic unsaturation are monomers, oligomers, polymers and mixtures thereof derived from the acrylates and methacrylates; olefinically unsaturated hydrocarbons, for example ethylene, propylene, butylene, isobutylene, 1-octene, 1-dodecene, 1-heptadecene, 1-eicosene and the like; vinyl compounds such as styrene, vinyl pyridine, 5-methyl-2 vinylpyridine, vinyl napthylene, alpha methylstyrene; vinyl and vinylidiene halides; acrylonitrile and methacrylonitrile; vinyl acetate and vinyl propionate; vinyl oxyethanol; vinyl trimethylacetate; vinyl hexonate; vinyl laurate; vinyl chloroacetate; vinyl stearate; methyl vinyl ketone; vinyl isobutyl ether; vinyl ethyl ether; compounds that have a plurality of ethylenic bonds such as those having conjugated double bonds such as butadiene, 2-chlorobutadiene, isoprene; and the like. Examples of preferable acrylates and methacrylates are disclosed in Skoultchi, U.S. Pat. No. 5,286,821 at column 3, lines 50 to column 6, line 12, incorporated herein by reference and Pocius, U.S. Pat. No. 5,681,910 at column 9, line 28 to column 12, line 25, incorporated herein by reference. More preferred olefinic compounds comprise methyl acrylate, methylmethacrylate, butylmethacrylate, tert-butylmethacrylate, 2-ethylhexyacrylate, 2-ethylhexylmethacrylate, ethylacrylate, isobornylmethacrylate, isobornylacrylate, hydroxyethylmethacrylate, glycidylmethacrylate, tetrahydrofurfuryl methacrylate, acrylamide, n-methylacrylamide, and other similar acrylate containing monomers. Also useful are the class of acrylate tipped polyurethane prepolymers available commercially from several sources, and prepared by reacting an isocyante reactive acrylate monomer, oligomer or polymer, such as a hydroxy acrylate, with an isocyanate functional prepolymer.

Where the organoborane complex is used in a composition that is used as an adhesive, acrylate and/or methacrylate based compounds are preferably used. The most preferred acrylate and methacrylate compounds include methylmethacrylate, butylmethacrylate, 2-ethylhexylmethacrylate, isobornylmethacrylate, tetrahydrofurfuryl methacrylate, and cyclohexylmethylmethacrylate.

In some embodiments polymerizable compositions including the organoborane complex may further comprise an effective amount of a compound that is reactive with an blocking agent so as to liberate the organoborane so as to initiate polymerization (a decomplexing agent). The blocking agent reactive compound liberates organoborane by reacting with the blocking agent, thereby removing the organoborane from chemical attachment with the blocking agent. Desirable amine reactive compounds are those materials that can readily form reaction products with blocking agent at or below and more preferably at room temperature about 20° C. to 22° C. so as to provide a composition that can be generally easily used and cured under ambient conditions. General classes of such compounds include acids, aldehydes, isocyanates, acid chlorides, sulphonyl chlorides, mixtures thereof and the like. Preferred amine reactive compounds are acids. Both Bronstead and Lewis acids may be used. Pocius, U.S. Pat. No. 5,718,977 describes the preferred acid compounds at column 9, line 1 to 15 incorporated herein by reference. The most preferred acids are acrylic acid and methacrylic acid.

Preferably the amount of polymerizable compounds in a polymerizable compositions or adhesive is about 20 percent by weight or greater based on the weight of the total composition, more preferably about 30 percent by weight or greater and most preferably about 40 percent by weight or greater. Preferably the amount of polymerizable compounds is about 95 percent by weight or less, preferably about 90 percent by weight or less and most preferably about 85 percent by weight or less. The amount of complex used in the composition can be any amount sufficient to initiate polymerization once the complex has disassociated at the desired speed of polymerization. At higher concentration of organoborane, the speed of polymerization is higher. Preferably the amount of organoborane complex is about 0.2 percent by weight or greater based on the weight of the total composition, preferably about 1.0 percent by weight or greater and most preferably about 2 percent by weight or greater.

Preferably the amount of organoborane complex present is about 8.5 percent by weight or less based on the total weight of composition. In those embodiments where a decomplexing agent is used, the amount of decomplexing agent (initiator) is that amount which is sufficient to initiate disassociation of the organoborane complex thereby causing the organoborane to initiate polymerization of the olefinically unsaturated compound. Preferably the amount of decomplexing agent is about 1 percent by weight or greater based on the weight of the total composition, more preferably about 1.5 percent by weight or greater and most preferably about 2 percent by weight or greater. Preferably the amount of decomplexing agent is about 8 percent by weight or less based on the weight of the total composition, more preferably about 6 percent by weight or less and most preferably about 4 percent by weight or less.

The organoborane complex may be readily prepared using known techniques. Typically, the blocking agent is combined with the organoborane in an inert atmosphere with slow stirring. An exotherm is often observed and cooling of the mixture is, therefore, recommended. If the ingredients have a high vapor pressure, it is desirable to keep the reaction temperature below about 70° C. to 80° C. Once the materials are well mixed the complex is permitted to cool to room temperature. No special storage conditions are required although it is preferred that the complex be kept in a capped vessel under an inert atmosphere, in a cool, dark location. Advantageously, the complexes of the invention can be prepared in the absence of organic solvents that would later have to be removed, although they could be prepared in solvent, if so desired. Solvents used in the preparation of the complexes should, preferably, be ones that do not coordinate the blocking agent, preferable solvents are for example, tetrahydrofuran or diethylether, or low molecular weight alkanes such as hexane or heptane.

The organoborane complexes are air stable. By "air stable" it is meant that when the complexes are stored in a capped vessel at room temperature (about 20° C. to 22° C.) and under otherwise ambient conditions (i.e., not under a vacuum and not in an inert atmosphere), the complexes remain useful as polymerization initiators for at least about two weeks, although the complexes may be readily stored under these conditions for many months.

By "air stable" it is also meant that the complexes are not pyrophoric. (When a few drops of the complex are placed on a paper towel under ambient conditions, the paper towel does not ignite, char or smoke.)

The organoborane complex can be used in polymerizable compositions that can be either one or two-part compositions depending upon the mechanism used to initiate polymerizations. In one embodiment the compositions are two-part compositions in which one-part contains the complexes having blocking agents as described herein and the other part contains the decomplexing agent (initiator). Polymerization may be initiated by contacting the two-parts of the composition. An advantage of this process is that polymerization can be initiated at, or even below, ambient temperatures. In this embodiment heat may be applied to the polymerizable composition to speed up initiation or polymerization. In another embodiment the polymerization composition may be initiated by heating the composition. In this embodiment no decomplexing agent (activator) is needed. When polymerization is activated by heating, the composition can be either a one-part or a two-part composition. The primary reason to use a two-part composition is to keep apart components of the composition which may be unstable in the presence of one another. Generally a one-part composition is preferred in this embodiment as the delivery equipment is less complex and costly and the need to properly ratio the components is eliminated.

In an embodiment where heat is used to activate the cure of the composition, the composition is exposed to a heat source which heats the composition to a temperature at or above the temperature at which the complex used in the composition decomposes to release the organoborane which then initiates free radical polymerization. Generally the composition is heated to a temperature which is less than the temperature at which the polymer formed undergoes degradation. The temperature at which the complex undergoes disassociation is related to the binding energy of the complex. At higher binding energies of the complex, higher temperatures are required to initiate polymerization. In an embodiment where the organoborane is activated thermally, the temperature at which the composition is heated to initiate polymerization is dictated by the binding energy of the complex. Generally the temperature used to initiate the polymerization by decomplexing the complex is about 30° C. or greater and preferably about 50° C. or greater. Preferably the temperature at which thermally activated polymerization is initiated is about 120° C. or less and more preferably about 100° C. or less. Any heat source which heats the composition to the desired temperature can be used provided the heat source does not negatively impact the components of the composition or its function. In this manner the composition may be contacted with the substrates either before or after the composition is exposed to heat. If the composition is heated prior to contact with the substrates, the composition should be contacted with the substrates before the composition has polymerized to the point at which the composition is no longer able to adhere to the substrates, this is usually the upper limit on the open time as defined hereinafter. It may be necessary in the thermally initiated reaction to control the oxygen content such that there is adequate oxygen to create favorable conditions for radical formation but not so much as to inhibit the polymerization.

The organoborane complex may be used in two-part polymerizable compositions or adhesive compositions that are uniquely suited for use with conventional, commercially available dispensing equipment for two-part adhesives. Once the two-parts have been combined, the composition should be used quickly, as the useful pot life (or open time) may be short depending upon the monomer mix, the amount of complex, and the temperature at which the bonding is to be performed. The adhesive composition is applied to one or both substrates and then the substrates are joined together with pressure to force excess composition out of the bond line. This also has the advantage of displacing composition that has been exposed to air and that may have begun to react. In general, the bonds should be made shortly after the composition has been applied, preferably within about 10 minutes. The typical bond line thickness is about 0.005 inches (0.13 mm) to about 0.03 inches (0.76 mm). The bonding process can easily be carried out at room temperature and to improve the degree of polymerization it is desirable to keep the temperature below about 40° C., preferably below about 30° C., and most preferably below about 25° C.

The bonds will cure to a reasonable green strength to permit handling of the bonded components within about 2 to 3 hours. Full strength will be reached in about 24 hours under ambient conditions; post-curing with heat (typically about 80° C.) may be used if desired.

When bonding fluoroplastics, it is advantageous to cool the initiator containing part of the two-part composition to about 0° C. to about 5° C. before adding the organoborane amine complex. The bond should be made as soon after the composition has been applied as practical; performing the bonding operation at less than about room temperature is also helpful.

The organoborane complex may also be used in compositions further comprising a variety of optional additives. One particularly useful additive is a thickener such as medium to high (about 10,000 to about 1,000,000) molecular weight polymethyl methacrylate which may be incorporated in an amount of about 10 to about 60 weight percent, based on the total weight of the composition. Thickeners may be employed to increase the viscosity of the composition to facilitate application of the composition.

Another particularly useful additive is an elastomeric material. The materials can improve the fracture toughness of compositions made therewith which can be beneficial when, for example, bonding stiff, high yield strength materials such as metal substrates that do not mechanically absorb energy as easily as other materials, such as flexible polymeric substrates. Such additives can be incorporated in an amount of about 5 percent to about 35 percent by weight, based on the total weight of the composition. Useful elastomeric modifiers include chlorinated or chlorosulphonated polyethylenes such as HYPALON 20 (commercially available from E. I. Dupont de Nemours & Co., Wilmington, Del.) and block copolymers of styrene and conjugated dienes (commercially available from Dexco Polymers under the Trademark Vector, and Firestone under the Trademark Stereon). Also useful, and even more preferred, are certain graft copolymer resins such as particles that comprise rubber or rubber-like cores or networks that are surrounded by relatively hard shells, these materials often being referred to as "core-shell" polymers. Most preferred are the acrylonitrile-butadiene-styrene graft copolymers available from Rohm and Haas. In addition to improving the fracture toughness of the composition, core-shell polymers can also impart enhanced spreading and flow properties to the uncured composition. These enhanced properties may be manifested by a reduced tendency for the composition to leave an undesirable "string" upon dispensing from a syringe-type applicator, or sag or slump after having been applied to a vertical surface. Use of more than about 20 percent of a core-shell polymer additive is desirable for achieving improved sag-slump resistance. Generally the amount of toughening polymer used is that amount which gives the desired toughness to the polymer or the adhesive prepared.

Another useful adjuvant is a cross-linking agent. Cross-linking agents can be used to enhance the solvent resistance of the adhesive bond or polymer composition, although certain compositions have good solvent resistance even in the absence of externally added cross-linking agents. Typically employed in an amount of about 0.2 to about 10 weight percent based on the total weight of the compositions, useful cross-linkers include the various diacrylates referred to above as possible acrylic modifying monomers as well as other materials. Particular examples of suitable cross-linking agents include ethylene glycol dimethacrylate, ethylene glycol diacrylate, triethyleneglycol dimethacrylate, diethylene glycol bismethacryloxy carbonate, polyethylene glycol diacrylate, tetraethylene glycol dimethacrylate, diglycerol diacrylate, diethylene glycol dimethacrylate, pentaerythritol triacrylate, trimethylolpropane triglycidyl ether, trimethylolpropane tris(2-methyl-1-aziridinepropionate, trimethylolpropane trimethacrylate, acrylate tipped polyurethane containing prepolymers, polyether diacrylates and dimethacrylates.

Peroxides may be optionally included (typically in an amount of about 2 percent by weight or less, based on the total weight of the composition), for example, to adjust the speed at which the compositions polymerize or to complete the polymerization.

Small amounts of inhibitors such as hydroquinone may be used, for example, to prevent or reduce degradation of the olefinic monomers during storage. Inhibitors may be added in an amount that does not materially reduce the rate of polymerization or the ultimate properties of an adhesive or other composition made therewith, typically about 10 to about 10,000 ppm based on the weight of the polymerizable monomers.

Other possible additives include non-reactive colorants, fillers (e.g., carbon black), etc. The various optional additives are employed in an amount that does not significantly adversely affect the polymerization process or the desired properties of compositions made therewith.

The organoborane complexes may also be used in polymerizable compositions that may be used in wide variety of ways, including as sealants, coatings, primers, to modify the surface of polymers, and injection molding resins. Such compositions may be used to form many items, including, inter alia, front end systems for vehicles and pipes. They may also be used as matrix resins in conjunction with glass and metal fiber mats such as in resin transfer molding operations. They may further be used as encapsulants and potting compounds such as in the manufacture of electrical components, printed circuit boards and the like. Quite desirably, they provide polymerizable adhesive compositions that can bond a diverse myriad of substrates, including polymers, wood, ceramics, concrete, glass and primed metals. Another desirable related application is their use in promoting adhesion of paints to low surface energy substrates such as polyethylene, polypropylene, polyethyleneterephthalate and polytetrafluoroethylene, and their co-polymers. In this embodiment the composition is coated onto the surface of the substrate to modify the surface to enhance the adhesion of the final coating to the surface of the substrate.

The organoborane complexes may be used in compositions that can be used in coating applications. In such applications the composition may further comprise a carrier such as water or a solvent. The coating may further contain additives well known to those skilled in the art for use coatings such as pigments to color the coating, inhibitors and UV stabilizers. The compositions may also be applied as powder coatings and may contain the additives well known to those skilled in the art for use in powder coatings.

The organoborane complexes may be used in compositions that can also be used to modify the surface of a polymeric molded part, extruded film or contoured object. Compositions of the invention can also be used to change the functionality of a polymer particle by surface grafting of polymer chains on to the unmodified plastic substrate.

Alternatively, the complexes of the present invention can be dissolved in a variety of solvents including water or organic solvents that provide a non acid containing environment and used as a primer. In this manner, the complex containing solution is applied to the surface that is to be used for adhesion, surface modification, or polymerization, and the solvent allowed to dry. The polymerizable monomer is then brought into contact with the complex on the surface and allowed to react for the purpose of promoting adhesion, or surface modification, or for initiating radical polymerization.

The organoborane complexes can be used in polymerizable compositions that are especially useful for adhesively bonding low surface energy plastic or polymeric substrates that historically have been very difficult to bond without using complicated surface preparation techniques, priming, etc. By low surface energy substrates is meant materials that have a surface energy of about 45 mJ/m$^2$ or less, more preferably about 40 mJ/m.sup.2 or less and most preferably about 35 mJ/m$^2$ or less. Included among such materials are polyethylene, polypropylene, acrylonitrile-butadiene-styrene, polyamides, syndiotactic polystyrene, olefin containing block co-polymers, and fluorinated polymers such as polytetrafluoroethlene (TEFLON) which has a surface energy of less than about 20 mJ/m$^2$. (The expression "surface energy" is often used synonymously with "critical wetting tension" by others.) Other polymers of somewhat higher surface energy that may be usefully bonded with the compositions of the invention include polycarbonate, polymethlmethacrylate, and polyvinylchloride.

The organoborane complexes can be used in polymerizable compositions that can be easily used as two-part adhesive. The components of the polymerizable compositions are blended as would normally be done when working with such materials. The decomplexing agent is usually included in this blend so as to separate it from the organoborane complex, thus providing one-part of the two-part composition. The organoborane complex of the polymerization initiator system provides the second part of the composition and is added to the first part shortly before it is desired to use the composition. The complex may be added to the first part directly or it may be pre-dissolved in an appropriate carrier such as methyl methacrylate.

It may be desirable to store the complexes apart from the monomers, oligomers or polymers to inhibit premature polymerization of the monomers, oligomers or polymers. The organoborane complexes have greatly enhanced stability when in the presence of monomers and in the absence of a decomplexing agent, such as an acid, and thus can be stored with the polymerizable components of the composition. Complexes in which the complexing amine nitrogen atom to boron atom ratio is greater than 1:1 may be sufficiently stable that they can be blended with polymerizable components in useful proportions. However, in such situations, the presence of additional non-polymerizing reactants (e.g., the organoborane liberator) may result in other, undesirable affects.

For a two-part adhesive to be most easily used in commercial and industrial environments, the ratio at which the two-parts are combined should be a convenient whole number. This facilitates application of the adhesive with conventional, commercially available dispensers. Such dispensers are shown in U.S. Pat. Nos. 4,538,920 and 5,082,147 (incorporated herein by reference) and are available from Conprotec, Inc. (Salem N.J.) under the trade name MIXPAC. Typically, these dispensers use a pair of tubular receptacles arranged side-by-side with each tube being intended to receive one of the two-parts of the adhesive. Two plungers, one for each tube, are simultaneously advanced (e.g., manually or by a hand-actuated ratcheting mechanism) to evacuate the contents of the tubes into a common, hollow, elongated mixing chamber that may also contain a static mixer to facilitate blending of the two-parts. The blended adhesive is extruded from the mixing chamber onto a substrate. Once the tubes have been emptied, they can be replaced with fresh tubes and the application process continued.

The ratio at which the two-parts of the adhesive are combined is controlled by the diameter of the tubes. (Each plunger is sized to be received within a tube of fixed diameter, and the plungers are advanced into the tubes at the same speed.) A single dispenser is often intended for use with a variety of different two-part adhesives and the plungers are sized to deliver the two-parts of the adhesive at a convenient mix ratio. Some common mix ratios are 1:1, 2:1, 4:1 and 10:1.

The part of the adhesive or polymerizable compositions which contain the organoborane complex preferably displays thermal stability at, or above, room temperature. Thermal stability as used herein means the organoborane complex does not disassociate and initiate polymerization of the olefinic unsaturated compounds present in the composition. Thermal stability can be measured by determining the temperature at which the viscosity of the composition begins to increase. Preferably the temperature at which the viscosity of the composition increases is greater than about 40° C., more preferably greater than about 60° C. and most preferably greater than about 80° C. The increase in viscosity indicates that the organoborane complex is disassociated and polymerization has been initiated. In the embodiment wherein the organoborane complex is used in a composition that is used as an adhesive, the adhesive preferably demonstrates a lap shear strength of about 750 p.s.i. or greater, more preferably about 1250 p.s.i. or greater and more preferably about 1500 p.s.i. or greater according to the following test procedure.

The adhesive components are mixed and applied to one or both substrates (1 in×4 in×⅛ in (25.4 mm×101.6 mm×3.2 mm) polypropylene coupons). Adhesive thickness is controlled by the addition of a few weight percent of glass beads between 0.005 to 0.030 inches in diameter (0.13 mm to 0.76 mm). The coupons are mated to provide 0.5 inch squared (161 mm$^2$) to 1.0 inch squared (645 mm$^2$) substrate overlap in a lap-shear testing configuration. The samples are held in place with metal binder clips to provide constant force and facilitate the elimination of air bubbles in the adhesive. The bonded samples were usually cured for at least about 24 hours before being mounted in a tensile testing apparatus fitted with a sample oven. The samples are evaluated at crosshead speeds of 0.05 (0.13 mm) and 0.5 (12.7 mm) inches per minute for room temperature and 110° C. testing conditions, respectively. Maximum load (pounds) to break are recorded and maximum stress (psi) is calculated by dividing this load by the overlap area (inches squared).

Preferably the open time of the adhesive is about 3 minutes or greater, more preferably about 5 minutes or greater, and most preferably about 8 minutes or greater. Preferably the open time of the adhesive is about 30 minutes or less, more preferably about 25 minutes or less, and most preferably about 20 minutes or less. Open time as used herein is the time between initiation of polymerization and the time at which the adhesive can no longer be applied and used as an adhesive. If the open time is too long, poor bond strength is observed. If the open time is too short, the composition polymerizes before a link up with the substrate can be achieved.

Preferably polymeric compositions have a suitable viscosity to allow application. Preferably the compositions have the viscosity of about 100 centipoise or greater, more preferable about 1,000 centipoise or greater and most preferably about 15,000 centipoise or greater. Preferably the adhesive compositions have a viscosity of about 100,000 centipoise or less, more preferably about 50,000 centipoise or less and most preferably about 30,000 centipoise or less.

Specific Embodiments

The following examples are included for illustrative purposes only and are not intended to limit the scope of the claims.

Three adhesive mixtures were prepared as follows.

Two component (part) adhesives are produced as described below. One component includes the organoborane complex (hardener) mixed with an acrylic resin. The other component is the acrylic resin possessing a decomplexing ingredient, for example methacrylic acid, that decomplexes the organoborane complex when mixed into the other component. Three separate adhesives were made using different blocking agents. Sample 1 uses a blocking agent in accordance with the present invention. Samples 2 and 3 use different blocking agents and are provided for comparative purposes.

Resin Component. The resin component for each sample comprises

| Material | Wt (g) |
|---|---|
| Methyl Methacrylate (MMA) | 58.8 |
| PARALOID ™ BTA 753 | 16.3 |
| HYPALON ™ 20 | 15.2 |
| Methoxyhdroquinone | 0.25 |
| Methacrylic Acid | 9.5 |

Hardners.

| | Wt (g) |
|---|---|
| Sample 1 | |
| TEB-2(2-Aminoethyl)Pyridine | 8.2 |
| MMA | 65.2 |
| PARALOID ™ BTA 753 | 25 |
| Sample 2 | |
| TEB-3-(methylamino)propylamine | 6.8 |
| MMA | 65.2 |
| PARALOID ™ BTA 753 | 25 |
| Sample 3 | |
| TNB-3-(methoxypropyl)amine | 9.5 |
| MMA | 65.2 |
| PARALOID ™ BTA 753 | 25 |

In all samples the number of moles of borane were held constant at 0.03188. The MMA used is a methacrylate monomer with 50 ppm MEHQ supplied by Rohm and Haas Company. PARALOID™BTA 753 is methacrylate-butadiene-styren copolymer supplied by Rohm and Haas Company. HALPALON™20 is chlorosulfonated polyethylene supplied by DuPont. The methacrylic acid and methoxyhdroquinone were supplied by Aldrich Chemical Company, Inc.

The procedure for making the hardeners was as follows. MMA was added to a 100 Long Jar made by FlackTeck Inc. The PARALOID™ BTA 753 was added to the MMA. The jar was sealed and placed in a FlackTek SpeedMixer™ DAC 400 FVZ by Hauschild Engineering. The material was mixed for 4 minutes at 2600 RPM. The temperature was observed to reach 45° C. The material was allowed to cool below 30° C. before the complexes were added. Once the material was cooled below 30° C., the complexes were added. The amount of complex added was controlled such that each sample contained the same number of moles of Borane. The material was then mixed for 1 minute at 1800 RPM.

The procedure for making the resin was as follows, using a dual asymmetric centrifugal FlackTek SpeedMixer™ DAC 400 FVZ by Hauschild Engineering. The HYPALON™ 20 was first combined with methyl methacrylate (MMA) into a preblend in a 40% HYPALON™ 20 to 60% MMA ratio using a roller mill. The HYPALON™ 20/MMA preblend was then added to a speed mixing cup followed by methyl methacrylate and methoxyhdroquinone (4-methoxyphenol (MEHQ)). PARALOID™ BTA-753 was then added to the speed mixing cup and immediately incorporated with the other ingredients by hand using a tongue depressor. The speed mixing cup was placed into the speed mixer and mixed three times consecutively for one minute at a speed of 1800 rpm. The temperature of each sample was checked after each mix using an infrared temperature probe and visually evaluated for homogeneity. If the sample was not visually homogeneous, additional one minute 1800 rpm mixing cycles were utilized until visual homogeneity was achieved. The temperature of each sample was kept below 130° F. by letting the sample sit at room temperature between additional mixes. After each sample was cooled to room temperature, methacrylic acid was charged into the speed mixing cup and immediately incorporated by hand using a tongue depressor. The speed mixing cup was then placed into the speed mixer and mixed twice for 1 minute at 1800 rpm.

Figure 1:
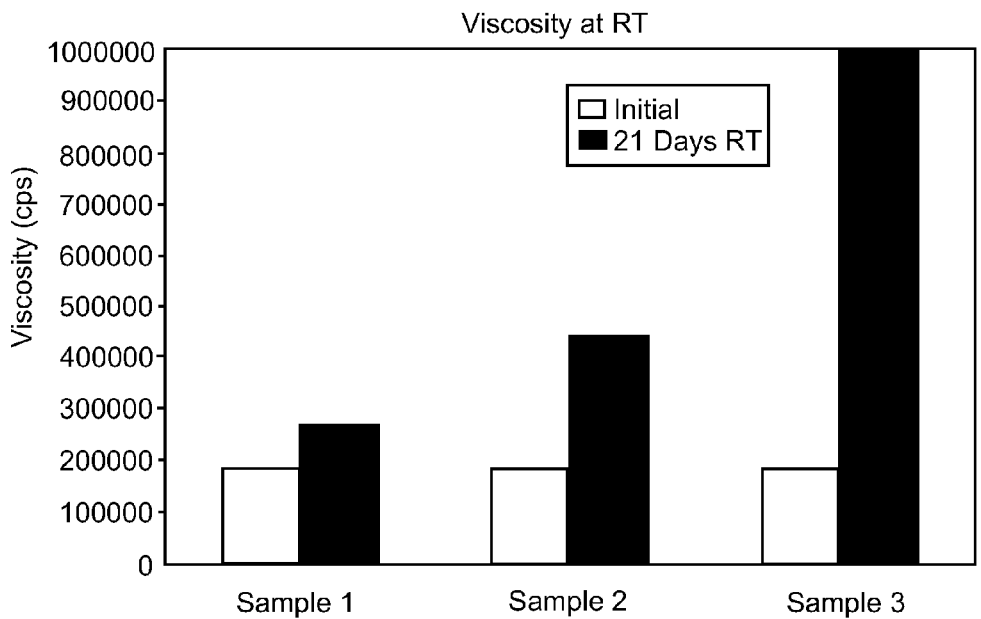
FIG. 1 is a graph showing viscosity measurements of various compounds.
Figure 2:
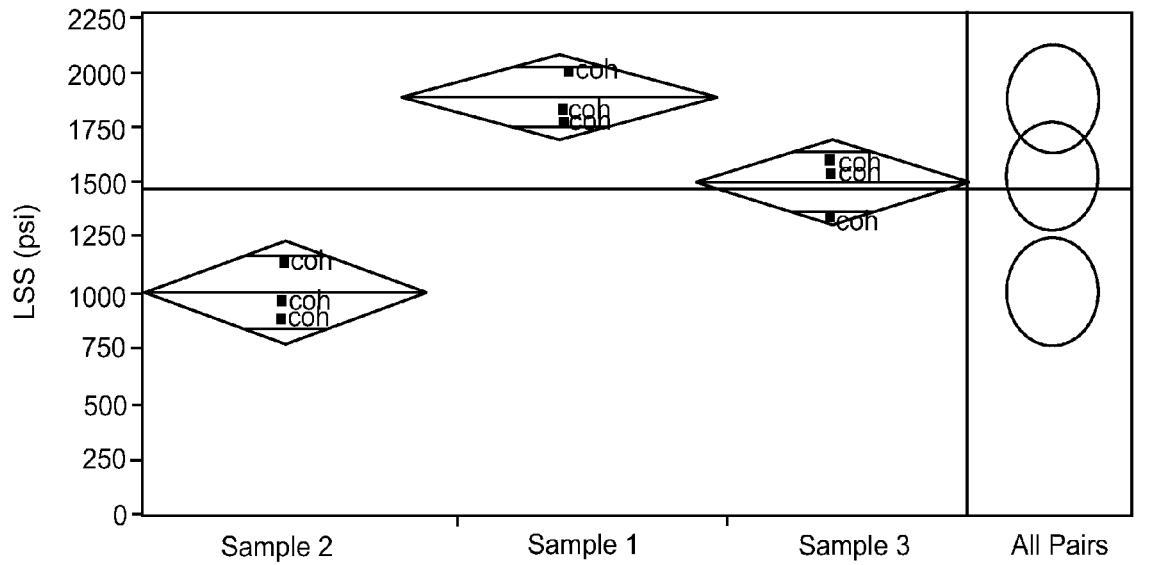
FIG. 2 is a graph showing lap shear test results of various compounds.

The two components of the adhesive composition are formulated to allow for a ratio of 1:1, 1:4, or 1:10 mixture of hardener:initiator, preferably 1:1. The adhesive may be mixed in the desired ratio in air, in a bag, or through a pressurized gun. The adhesive is applied to a polypropylene test strip 1 inch (25.4 mm) wide with a ½ inch (12.7 mm) overlap and is tested for adhesive strength as described previously. The lap shear test results are shown in FIG. 2. Further, the viscosity of the samples was measured. Both initial viscosity was measured and the viscosity after 21 days at room temperature. The results of the measurements are shown in FIG. 1. As is readily apparent from FIGS. 1 and 2, the preferred blocking agent showed and increase in lap shear strength and an improved shelf life—evidenced by having lower viscosity over the 21 day period.

Finally, calculated complex energies for several blocking agents, including the preferred blocking agent, as well as those blocking agents of the comparative samples are shown in FIG. 3.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An organoborane complex comprising:
an organoborane compound and a blocking agent, wherein the blocking agent corresponds to the formula

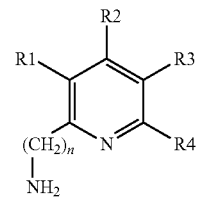

wherein n is 1-3, and R1-R4 are hydrogen or form a quinolin or isoquinolin-ring structure together with the pyridine ring.

2. The organoborane complex as set forth in claim 1 wherein n is 2.

3. The organoborane complex as set forth in claim 2, wherein the organoborane compound corresponds to formula $B\text{-}(R^2)_3$, wherein $R^2$ is a $C_{1\text{-}10}$ alkyl, $C_{3\text{-}10}$ cycloalkyl, or two or more $R^2$ are combined to form a cycloaliphatic ring structure.

* * * * *